US008884248B2

(12) United States Patent
Mulders et al.

(10) Patent No.: US 8,884,248 B2
(45) Date of Patent: Nov. 11, 2014

(54) FORMING A VITRIFIED SAMPLE FOR ELECTRON MICROSCOPY

(71) Applicant: FEI Company, Hillsboro, OR (US)

(72) Inventors: Johannes Jacobus Lambertus Mulders, Eindhoven (NL); Rudolf Johannes Peter Gerardus Schampers, Tegelen (NL); Petrus Hubertus Franciscus Trompenaars, Tilburg (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/766,221

(22) Filed: Feb. 13, 2013

(65) Prior Publication Data

US 2013/0205808 A1 Aug. 15, 2013

Related U.S. Application Data

(60) Provisional application No. 61/597,955, filed on Feb. 13, 2012.

(30) Foreign Application Priority Data

Feb. 13, 2012 (EP) .................................. 121551121

(51) Int. Cl.
*H01J 37/26* (2006.01)
*G01N 1/00* (2006.01)
*G01N 1/42* (2006.01)
*F25D 31/00* (2006.01)
*B01L 7/00* (2006.01)

(52) U.S. Cl.
CPC *F25D 31/00* (2013.01); *G01N 1/00* (2013.01); *G01N 1/42* (2013.01); *B01L 7/50* (2013.01)
USPC .................... 250/443.1; 250/440.11; 250/311

(58) Field of Classification Search
USPC ............ 250/306, 307, 309, 310, 311, 440.11, 250/441.11, 442.11, 443.1, 492.1, 492.2, 250/492.21, 492.3
See application file for complete search history.

(56) References Cited

U.S. PATENT DOCUMENTS 5,364,756 A 11/1994 Livesey et al.
5,435,850 A 7/1995 Rasmussen
(Continued)

OTHER PUBLICATIONS

Berriman, John, et al., 'Analysis of transient structures by cryo-microscopy combined with rapid mixing of spray droplets,' Ultramicroscopy, Dec. 1, 1994, pp. 241-252, vol. 56, No. 4.
Unknown, 'Application note 3D Cryo-DualBeam™,' 4 pgs, retrieved Jan. 15, 2013, http://www.fei.com/uploadedFiles/Documents/Content/2006_06_3D_Cyro_DualBeam_mb.pdf.
Unknown, 'Graphene Transmission Electron Microscopy Support Films,' 2 pgs, retrieved Feb. 12, 2013, http://www.graphene-supermarket.com/images/XC/TEM/GrapheneTEMgrids-General%20info.pdf.

(Continued)

*Primary Examiner* — Nicole Ippolito
(74) *Attorney, Agent, or Firm* — Scheinberg & Associates, PC; John E. Hillert; Michael O. Scheinberg

(57) ABSTRACT

The invention relates to a method of forming a vitrified sample on a sample holder for inspection in an electron microscope. It is known to spray a solution on a grid and then immerse the grid in a cryogenic liquid, such as ethane or liquid nitrogen. The invention proposes to spray small droplets of the liquid on a cryogenic surface, such as a grid or a sample holder in vacuum. The liquid forms vitrified sample material when hitting the surface due to the low temperature of the grid or sample holder.
A lamella may be excavated from the thus formed sample material, to be studied in a TEM, or the vitrified sample material may be directly observed in a SEM. In an embodiment the material may be sprayed on a cryogenic liquid, to be scooped from the liquid and placed on a grid.

20 Claims, 3 Drawing Sheets

(56) References Cited

U.S. PATENT DOCUMENTS

| | | | |
|---|---|---|---|
| 5,780,295 | A | 7/1998 | Livesey et al. |
| 6,194,136 | B1 | 2/2001 | Livesey et al. |
| 2008/0293832 | A1 | 11/2008 | Yokoi et al. |
| 2009/0000400 | A1* | 1/2009 | Hayles et al. ............... 73/863.12 |
| 2010/0316811 | A1 | 12/2010 | Mulders |
| 2011/0098960 | A1 | 4/2011 | Mizuochi |
| 2012/0003394 | A1* | 1/2012 | Mulders et al. ............... 427/551 |
| 2013/0091875 | A1* | 4/2013 | Hartfield ........................... 62/62 |

OTHER PUBLICATIONS

Lu, Zonghuan, et al., 'Monolithic microfluidic mixing—spraying devices for time-resolved cryo-electron microscopy,' Journal of Structural Biology, Aug. 14, 2009, pp. 388-395, vol. 168.

White, H.D., 'A second generation apparatus for time-resolved electron cryo-microscopy using stepper motors and electrospray,' Journal of Structural Biology, 2003, pp. 246-252, vol. 144.

* cited by examiner

FORMING A VITRIFIED SAMPLE FOR ELECTRON MICROSCOPY

This Application claims priority from U.S. Provisional Application 61/597,955, filed Feb. 13, 2012, which is hereby incorporated by reference.

The invention relates to a method of forming an image of a vitrified sample, the method comprising:
Providing an aqueous solution comprising sample material,
Spraying the aqueous solution on a surface,
Solidifying the solution by cooling the solution,
Forming an image of the sample material in a sample chamber of a charged particle microscope.

Such a method is known from "A second generation apparatus for time-resolved electron cryo-microscopy using stepper motors and electrospray", H. D. White et al., J. Struct. Biol 144 (2003), pp 246-252, further referred to as White [-1-].

When studying (imaging, analyzing) a sample in a transmission electron microscope (TEM) a beam of energetic electrons with a selectable energy of, for example, between 60 keV and 300 keV, irradiates a sample. The sample should be sufficiently thin so that a large portion of the electrons pass through the sample, to be imaged/detected. The imaging may for example comprise imaging the electrons on a fluorescent material, or imaging the electrons on a detector comprising, for example, a CCD or CMOS chip.

As known to the skilled person similar imaging or analysis can be performed by scanning a beam of energetic charged particles (electrons, ions, clusters) over the sample and observing the radiation emerging from the sample in response to the impinging charged particles. Such a study is then performed in the evacuated sample chamber of an apparatus equipped with a Scanning Electron Microscope (SEM) column and/or a Focused Ion Beam (FIB) column.

For biological material it is necessary to study for example tissue in the harsh environment of an electron microscope, i.e. in vacuum and at high radiation levels. To that end the sample material is often cooled to a cryogenic temperature. Cooling biological material to cryogenic temperature involves more than just cooling the material, as cooling typically results in damage of the sample material (cells, bacteria, viruses, or the like) by the formation of ice needles. As known to the person skilled in the art the sample material should be embedded in vitrified ice, which is an amorphous form of ice. Vitrified ice is formed by cooling an aqueous solution at a rate in the order of $10^5$ K/s to a temperature of less than the glass transition temperature of approximately 165 K. As an alternative vitrification is performed at a pressure of approximately 2100 bar at a cooling rate of "only" approximately 600 K/s. As the cooling rate is lower, thicker vitrified samples can be formed in this so-called High Pressure Freezing (HPF) process.

A cryogenic sample in vitrified ice is for example formed by applying a thin layer of an aqueous solution on a carrier, for example a TEM grid. Excess water is then removed by blotting, and the remaining carrier with the aqueous solution is then plunged in a cryogenic fluid, such as ethane or liquid nitrogen. An example of an apparatus to perform this method is commercially available under the name Vitrobot, and manufactured by FEI Company, Hillsboro, Oreg., USA.

In the method described by White [-1-] an aqueous solution comprising sample material is sprayed on the carrier while the carrier (still at room temperature) is moving to be plunged in the cryogenic fluid: in this way processes can be arrested as they are frozen shortly after being sprayed on the carrier.

The invention intends to provide an alternative method to form cryogenic samples.

To that end the method according to the invention is characterized in that the surface on which the solution is sprayed has a cryogenic temperature, as a result of which a vitrified sample is formed on the surface at the moment the droplets hit the surface, and that the droplets are sprayed on the cryogenic surface while in the sample chamber of the charged particle microscope.

The invention is based on the insight that, when spraying small droplets on a cryogenic surface, the droplets cool fast enough to solidify in the form of amorphous ice, thus forming a vitrified sample. As this is done in situ (in the charged particle microscope) the sample is prepared quick and in an environment where no ice can grow on the now cryogenic sample.

It is noted that it is estimated that for droplets with a diameter of more than 10 μm, the cooling of at least part of the droplet is too slow to form vitrified ice. Preferably a part of the droplets should thus have a diameter of less than 10 μm, more preferably less than 2 μm. The exact maximum size of the droplets depends on the presence of, for example, cryo-protectants, such as glycerol, glucol, or certain anti-freeze proteins. In the presence of such a cryo-protectant the diameter may be larger.

It is noted that at impact the presumably round droplet deforms to a shape that has a larger surface-to-volume ratio and less 'thickness', thus enhancing the cooling rate.

In an embodiment of the method according to the invention the aqueous solution is sprayed on a sample holder, the sample holder kept at a cryogenic temperature by contact with a cryogenic holding device.

The sample holder, for example a TEM grid or a SEM stub holder, is preferably held by a cryogenic holding device, as a result of which the sample holder is cooled to a cryogenic temperature. In this way a sample can be prepared on the sample holder, and then the sample holder can be removed from the holding device, to be exchanged for another sample holder for forming another sample.

The sample holder can be attached to the holding device with, for example, electrostatic forces. However, other attachment methods, such as clamping, may be used as well.

In a preferred embodiment the sample holder is a sample holder equipped to be used in an electron microscope.

In this embodiment the sample holder is the sample holder used in a SEM (often referred to as a stub holder) or a so-named grid for a TEM.

In another embodiment the vitrified sample is machined by slicing with, for example, a cryoultramicrotoom or by milling with a focused ion beam, thereby forming a sample in the form of a lamella. Samples in the form of a thin lamella's, with a thickness of less than 1 μm, more preferably less than 200 nm, are used in Transmission Electron Microscopy. The thus formed lamella's may be mounted on a sample holder by attaching it to a manipulator that transports it to, for example, a TEM sample holder (a "grid") and then attach it to the sample holder by, for example, beam induced deposition (BID).

In yet another embodiment of the method according to the invention the aqueous solution is sprayed from a mixer. Such a mixer is known from "Monolithic microfluidic mixing—spraying devices for time-resolved cryo-electron microscopy", Z. Lu et al., J. Struct. Biol. 168 (2009), pages 388-395, further referred to as Lu [-2-]. Such a mixer enables the mixing of chemicals with the aqueous solution milliseconds before the sample material is sprayed on the cryogenic surface, where the chemical reactions are arrested.

This mixing may especially be attractive for embedding cells (or parts thereof) in water with cryoprotectant. When adding the cryo-protectant to the water just before spraying, the cryo-protectant does not have time to enter the cell, and therefore the cell is seen in its natural condition, even when the water outside the cell contains a cryo-protectant.

In still another embodiment of the method according to the invention the sample material is sprayed on a solid or liquid that melts, evaporates or sublimates at a temperature below the glass transition temperature, the solid or liquid together with the sample material is put on a sample carrier, and after putting the solid or liquid together with the sample material on the sample carrier the solid or liquid is removed.

Removal can take the form of evaporation, sublimation, or removing the (cryogenic) liquid by e.g. blotting.

When working in an environment of dry nitrogen, the aqueous solution can be sprayed on liquid nitrogen, preferably non-boiling. Similarly ethane can be used, in either an environment of dry ethane or nitrogen.

It is noted that this embodiment may be incompatible with a vacuum environment, as typically high vapor pressure occurs during removal of the solid or liquid.

The invention is now elucidated using figures, in which identical reference numerals indicate corresponding features.

BRIEF DESCRIPTION OF THE DRAWINGS

To that end.

EMBODIMENT 1

Figure 1:
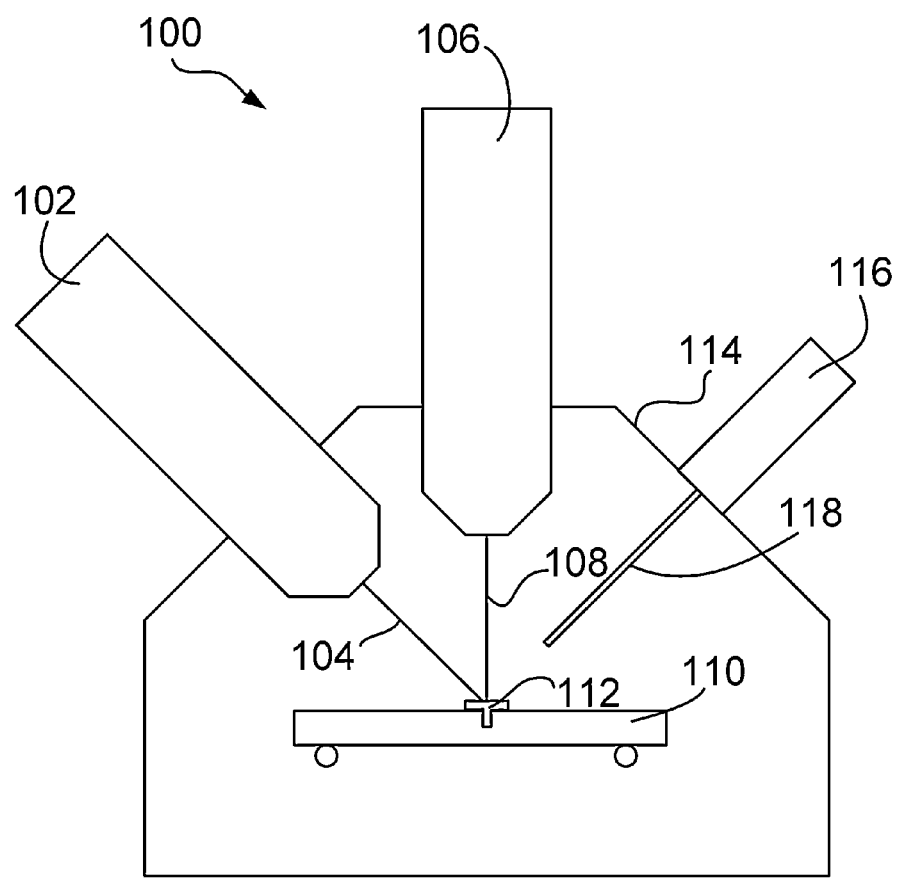
FIG. 1 schematically shows a charged particle apparatus equipped with a Gas Injection System.

FIG. 1 schematically shows a first embodiment. A charged particle apparatus 100 equipped with a focused ion beam column (FIB column) 102 for producing a beam of ions 104 and a scanning electron microscope column (SEM column) 106 for producing a beam of electrons 108. Such a charged particle apparatus is commercially available as, for example, a 3D Cryo DualBeam™ apparatus, and sold by FEI Company, Hillsboro, Oreg., USA. An application note describing the apparatus is available on the internet, see [-3-].

Such an instrument is equipped with a sample stage 110 that is equipped to be held at a cryogenic temperature, typically around −160° C. The sample stage is equipped to hold sample holders 112 (also known as "stubs") on which a sample is sprayer or otherwise mounted. The stage is positioned in an evacuable sample chamber 114. A sample mounted on the stage can be machined (milled, sputtered) by the focused ion beam 104 produced by the FIB column, and imaged using the focused electron beam 108. Secondary radiation emerging from the sample as a result of the impinging charged particles is detected by one or more detectors (not shown), such as a secondary electron detector or an X-ray detector.

Where prior art methods required that a sample was loaded in the vacuum chamber by placing the sample mounted on a sample holder on the sample stage, the method according to the invention forms the sample "in-situ" by spraying a jet of small droplets on the cryogenic sample holder 112

First experiments used a modified Gas Injection System (GIS) 116 as described in U.S. Pat. No. 5,435,850 to FEI Co, Hillsboro, USA. Such a GIS incorporates a hollow metal needle 118 with a diameter of between 1 and 2 millimeter and one end is positioned close to the sample stage. The other end is via a plunger connected to a heatable volume (the "crucible") where normally the material to be injected resides at a pressure between 0.1 to 100 mbar (typically less than 1 mbar). It is noted that the material to be injected is turned in a gaseous product by evaporation or sublimation. The plunger is opened to inject gas, and closed to stop doing so. The GIS was modified, the modifications involving:

locating an aperture with a diameter of 200 μm between the plunger and the crucible the needle was removed from the sample holder the crucible plunger area was loaded with a suspension comprising cells of baker's yeast (ca 1 ml)

Figure 3:
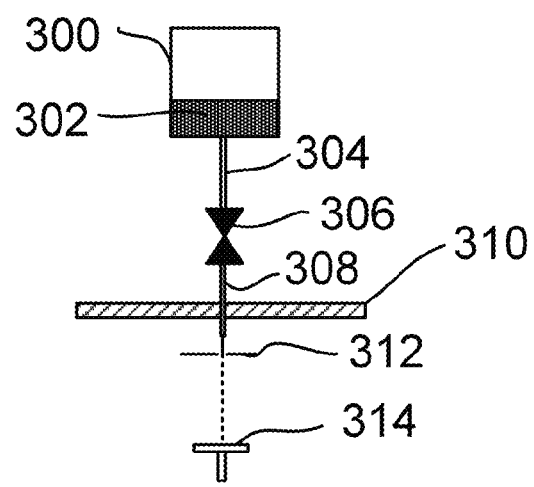
FIG. 3 shows a shallow cup-shaped TEM sample holder for use with embodiment 5

The resultant modified GIS is schematically shown in FIG. 3. Crucible 300 is partly filled with solution 302 comprising sample material. Tube 304 connects the crucible with a valve 306. Through this valve liquid enters a tube 308 that feeds through the vacuum wall of the electron microscope 310. The liquid is then atomized when passing through a 200 μm aperture in diaphragm 312. It is noted that a pressure difference is present between the crucible and the aperture in the diaphragm, as the crucible is at an internal pressure of between 0.1 to 100 mbar, while the aperture connects to the evacuated volume in which the sample holder resides. The atomized suspension is then sprayed on sample holder 314, that is kept at a temperature of, for example, −160° C. The distance between the aperture in diaphragm 312 and sample holder 314 is approximately 5 cm.

These modifications enabled the GIS to spray small volumes of the suspension by shortly opening and almost immediately closing the GIS. As a result of this a small amount of cell suspension formed of many tiny droplets was "sneezed" upon the sample holder.

Figure 2A:
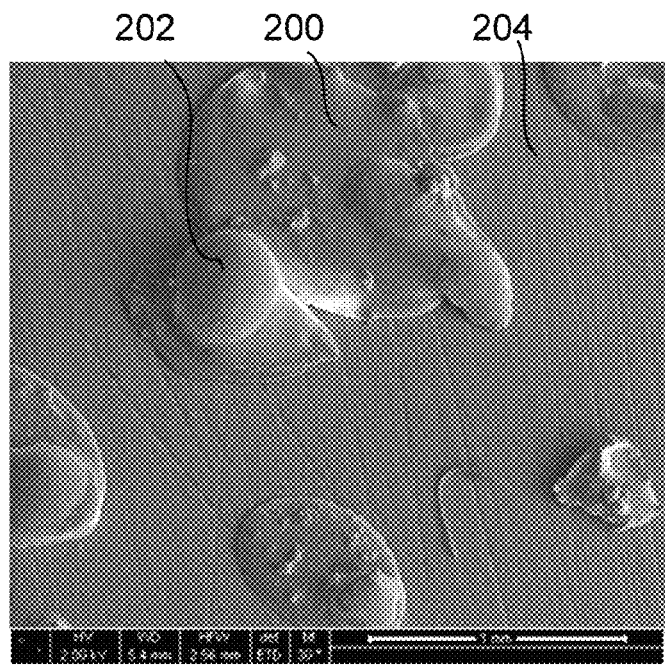
FIGS. 2A, 2B and 2C show SEM images of vitrified sample material.
Figure 2B:
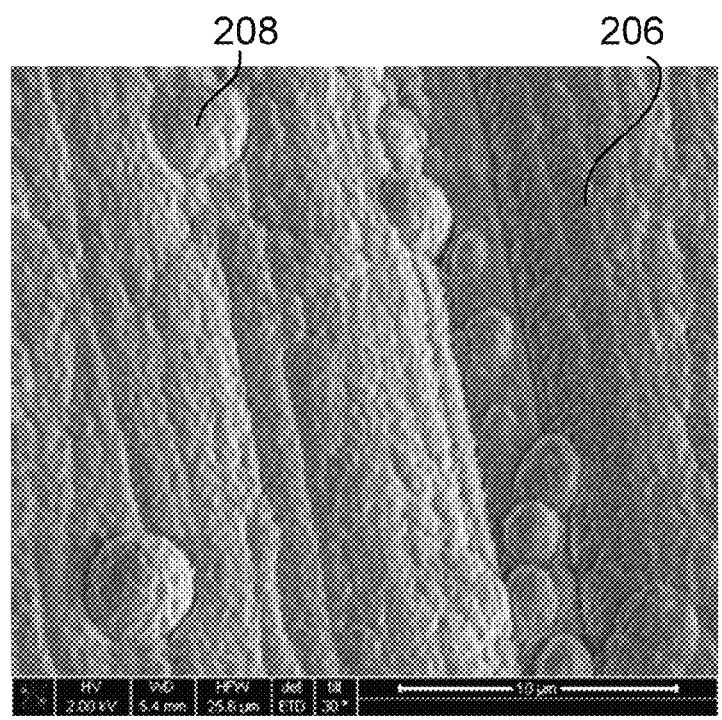
Figure 2C:
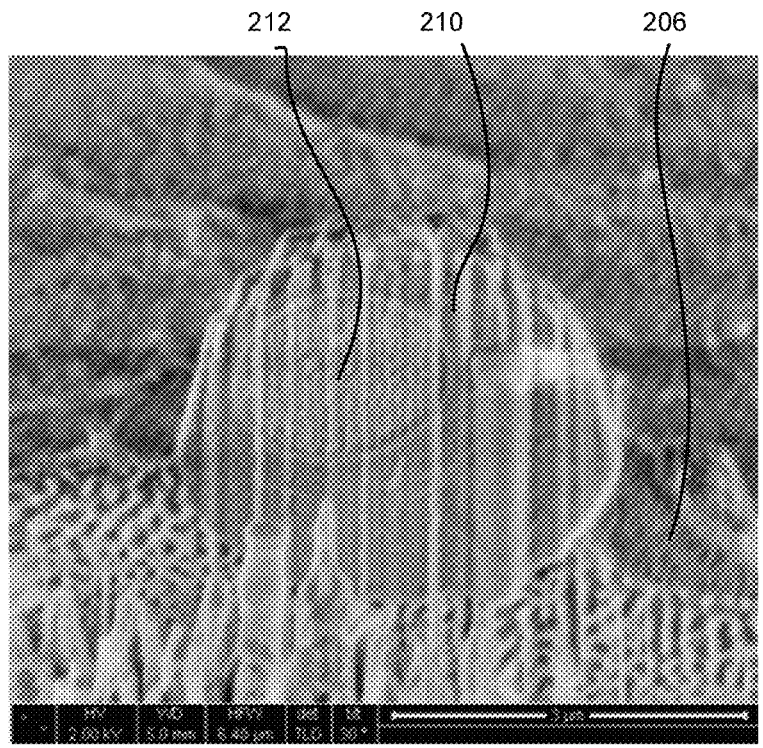

The result of the spraying is shown in FIG. 2A and (more detailed) FIG. 2B. FIG. 2A shows a field of view of approximately 2½×2½ mm². It shows a few large droplets 200 and 202. Droplet 200 seems to be flattened at impact. The area 204 between the obviously covered part turns out to be covered by a very thin layer of ice, as shown in FIG. 2B. FIG. 2B shows a field of view of 25×25 μm², showing a thin layer 206 of ice in which cells 208 are embedded. FIG. 2C shows an even further enlargement showing a field of view of approximately 6×6 μm², in which, using a focused ion beam, a part of a cell is removed so that a cross section is visible. It shows the amorphous ice matrix 206 and the cross section 210 of a cell, showing among other its nucleus 212. No sign of ice needles is found. It is expressly noted that these are the results of first, very crude, experiments, and that the limitations of these pictures should not be taken as limitations of the methods according to the invention.

EMBODIMENT 2

In a second embodiment the suspension is not sprayed on the cold surface through a needle, but by a mixer like the one described by Lu [-2-] in its FIG. 1 and accompanying text. In this way changes in the fluid can be made shortly before spraying the suspension on the cryogenic surface.

It is noted that also a heater can be incorporated to hold the suspension in the mixer at a desired temperature of, for example, 37° C., or a desired lower or higher temperature.

It is further noted that the use of a gas for atomizing the fluid (suspension) implies that this embodiment is suited for use in a protective atmosphere and less suited for use in a vacuum. However, provided that the pressure bursts of the gas atomizing the suspension are modest and the vacuum system is tolerant to pressure bursts, such as used in for example an Environmental SEM, this embodiment may be used to spray the suspension on the sample holder in situ, that is: in the evacuated sample chamber of an Environmental SEM or another charged particle instrument equipped to deal with such pressures.

EMBODIMENT 3

In a third embodiment the suspension is sprayed on the surface using electrospraying, as described by, for example, White [-1-]. Although White [-1-] proposes electro-spraying in a protective environment only, the person skilled in the art will realize that this can take place in a vacuum as well, i.e. in the specimen chamber of an electron microscope or, more general, of a charged particle apparatus.

It is noted that the opening from which the suspension emerges can be a nozzle mounted on the mixer of embodiment 2, leading to a hybrid embodiment.

EMBODIMENT 4

In this embodiment the aqueous solution is sprayed on a cryogenic liquid or cryogenic solid. The liquid or solid is characterized in that it can be removed at a temperature below the glass transition temperature of water. This removal may be done by evaporating the fluid, by sublimation, by draining, or any other way. The frozen droplets can then be left on for example a—originally submerged—sample holder, or be scooped from the liquid. The cryogenic liquid can be for example liquid nitrogen or ethane.

EMBODIMENT 5

This embodiment is alike to embodiment 4, but here a TEM sample grid comprising a grid with a thin film is kept on top of the fluid.

TEM carbon grids are commercially available where a carrier grid is used to support a carbon film of only several micrometers thick, or even comprising a graphene film (see for example the brochure of Graphene Laboratories Inc., Calverton, N.Y., USA. As such a thin carbon film hardly interacts with a beam of electrons, a sample placed on this film can be well imaged. Similarly grids with a thin $Si_3N_4$ film are commercially available.

The problem when using such a grid for the method according to the invention is that the heat capacity of the thin film is insufficient to cool the droplets to a temperature below the glass transition temperature.

Embodiment 5 solves this by keeping one side of the film in contact with a cryogenic liquid. In this way the thin carbon film is kept at a low temperature even when larger amounts of water are sprayed on the film.

It is noted that similarly the grid can be placed on a cold metal surface, but that often the film is then frozen to the metal surface.

It is further noted that the grid can be formed as a shallow cup, minimizing the risk that some of the cryogenic liquid sloshes over the film. Such a cup can be made to float upon the cryogenic liquid.

EMBODIMENT 6

In a sixth embodiment a cryogenic surface is covered by vitrified sample material by one of the methods described earlier, after which samples, such as lamella, are formed from the vitrified sample material by excavating the samples or lamella using a focused ion beam and freeing the samples or lamellas from the cryogenic surface and transporting them to a (cryogenic) sample carrier, for example a TEM grid.

It is noted that prolonged spraying of the solution on the cryogenic surface can lead to a thick layer of sample material from which the lamella can be excised.

It is further noted that other techniques, such as fluorescent techniques, can be used to identify areas of interest on the layer of sample material, after which lamella or samples can be taken from these areas.

literature:
[-1-] "A second generation apparatus for time-resolved electron cryo-microscopy using stepper motors and electrospray", H. D. White et al., J. Struct. Biol 144 (2003), pp 246-252.
[-2-] "Monolithic microfluidic mixing-spraying devices for time-resolved cryo-electron microscopy", Z. Lu et al., J. Struct. Biol. 168 (2009), pp 388-395.
[-3-] Application note 3D Cryo-DualBeam™, FEI Co., Hillsboro, Oreg., USA: http://www.fei.com/uploadedFiles/Documents/Content/2006_06_3D_Cyro_DualBeam_mb.pdf
[-4-] Gas Injection System, U.S. Pat. No. 5,435,850.
[-5-] Brochure of Graphene Laboratories Inc, Calverton, N.Y., USA: http://www.graphene-supermarket.com/images/XC/TEM/GrapheneTEMgrids-General%20info.pdf

We claim as follows:

1. A method of forming an image of a vitrified sample in a particle-optical apparatus, the particle-optical apparatus equipped with an evacuable sample chamber, the method comprising:
   providing an aqueous solution comprising sample material;
   spraying droplets of the aqueous solution on a surface, the surface being a cryogenic surface in the evacuated sample chamber of the particle-optical apparatus;
   forming a vitrified sample by rapidly cooling the solution, the vitrified sample being formed on the surface at the moment the droplets hit the surface; and
   forming an image of the vitrified sample with a particle-optical apparatus.

2. The method of claim 1 in which at least part of the droplets have a diameter of less than 10 µm, as a result of which the at least part of the droplets form the vitrified sample.

3. The method of claim 1 in which the aqueous solution is sprayed on a sample holder, the sample holder kept at a cryogenic temperature by contact with a cryogenic holding device.

4. The method of claim 3 in which the cryogenic holding device attracts the sample holder by electrostatic forces.

5. The method of claim 3 in which the particle-optical apparatus is equipped with an electron microscope column or an ion beam column.

6. The method of claim 1 further comprising forming a sample in a shape of a lamella by machining the vitrified sample, wherein machining the vitrified sample comprises slicing with a cryoultramicrotoom or milling with an ion beam.

7. The method of claim 1 in which the aqueous solution is sprayed 1 from a mixer equipped to mix fluids and to spray the aqueous solution on the surface.

8. The method of claim 1 in which the aqueous solution is sprayed on the surface using electro-spraying.

9. The method of claim 1 in which the sample material is sprayed on the cryogenic surface using an injection system equipped with a capillary.

10. The method of claim 1 in which the forming a vitrified sample by rapidly cooling the solution and the forming an image of the vitrified sample with a charged particle apparatus occurs in the same particle-optical apparatus, without exposing the sample to an elevated pressure between the forming a vitrified sample by rapidly cooling the solution and the forming an image of the vitrified sample.

11. A charged particle apparatus comprising:
a stage positioned in an evacuable sample chamber;
sample holders for holding a surface, the sample holders attached to the stage, the sample holders configured to be kept at a cryogenic temperature;
a sprayer configured to spray an aqueous solution comprising sample material onto the surface such that a vitrified sample forms;
a particle-optical column configured to direct at least one beam of particulate radiation onto the vitrified sample such that radiation is emitted from the vitrified sample; and
one or more detectors arranged to detect at least a portion of the emitted radiation.

12. The apparatus of claim 11 in which the sprayer comprises electro-spraying, spraying from a mixer equipped to mix fluids and to spray the aqueous solution on the surface, or using an injection system equipped with a capillary.

13. The apparatus of claim 11 in which the sample holders are kept at the cryogenic temperature through contact with a cryogenic holding device.

14. The apparatus of claim 13 in which the cryogenic holding device attracts the sample holder by electrostatic forces.

15. The apparatus of claim 11 in which the particle-optical column comprises an ion beam column or an electron microscope column.

16. The apparatus of claim 13 in which the at least one beam of particulate radiation can be used to process or image the vitrified sample.

17. The apparatus of claim 11 in which the one or more detectors comprise secondary electron detectors or X-ray detectors.

18. The apparatus of claim 11 in which the sprayer is configured to spray the aqueous solution comprising the sample material as droplets, at least part of the droplets having a diameter of less than 10 μm, as a result of which the at least part of the droplets form the vitrified sample.

19. The apparatus of claim 16 configured to form the vitrified sample and image the vitrified sample with the at least one beam of particulate radiation in the same particle-optical apparatus such that the vitrified sample is not exposed to an elevated pressure between forming the vitrified sample and imaging the vitrified sample.

20. The apparatus of claim 11 further comprising a cryoultramicrotom configured to machine the vitrified sample to form a sample in the form of a lamella.

* * * * *